US006656124B2

(12) United States Patent
Flesch et al.

(10) Patent No.: US 6,656,124 B2
(45) Date of Patent: Dec. 2, 2003

(54) STACK BASED MULTIDIMENSIONAL ULTRASONIC TRANSDUCER ARRAY

(75) Inventors: Aimé Flesch, Andrésy (FR); An Nguyen-Dinh, Valleres (FR)

(73) Assignee: Vermon, Tours Cedex (FR)

( * ) Notice: Subject to any disclaimer, the term of this patent is extended or adjusted under 35 U.S.C. 154(b) by 94 days.

(21) Appl. No.: 09/976,294

(22) Filed: Oct. 15, 2001

(65) Prior Publication Data

US 2003/0073906 A1 Apr. 17, 2003

(51) Int. Cl.[7] .................................................. A61B 6/00
(52) U.S. Cl. ....................................................... 600/459
(58) Field of Search ................................. 310/344, 336, 310/322, 334; 600/437, 459, 460

(56) References Cited

U.S. PATENT DOCUMENTS

| 5,605,154 A | * | 2/1997 | Ries et al. | 600/444 |
| 5,744,898 A | * | 4/1998 | Smith et al. | 310/334 |
| 5,834,880 A | * | 11/1998 | Venkataramani et al. | 310/334 |
| 5,957,851 A | * | 9/1999 | Hossack | 600/459 |
| 6,441,538 B1 | * | 8/2002 | Spigelmyer | 310/328 |

* cited by examiner

*Primary Examiner*—Francis J. Jaworski
*Assistant Examiner*—Maulin Patel
(74) *Attorney, Agent, or Firm*—Larson & Taylor, PLC

(57) ABSTRACT

Multilayer piezoelectric fabrication methods are used to produce nD (e.g., 1.5D and 2D) ultrasonic transducer arrays. One embodiment concerns a 1.5 linear transducer in which impedance compensation is provided between the elemental transducers forming the array by varying the number of layers in each row of transducers. In another embodiment, a 2D transducer array is provided wherein elemental transducers are produced by dicing a conventional multilayer actuator to form equal sized elements which are embedded in a polymer matrix.

20 Claims, 10 Drawing Sheets

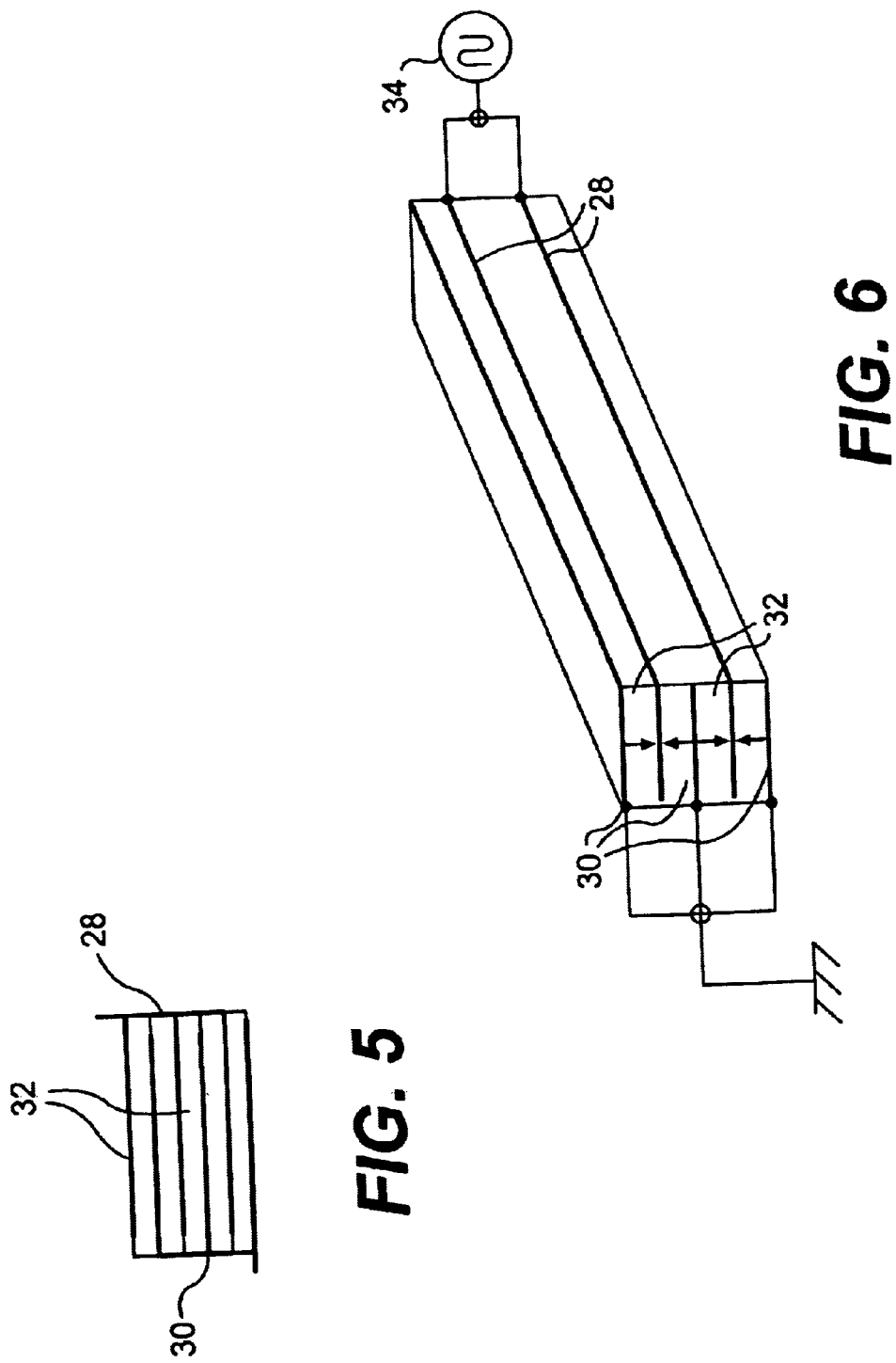

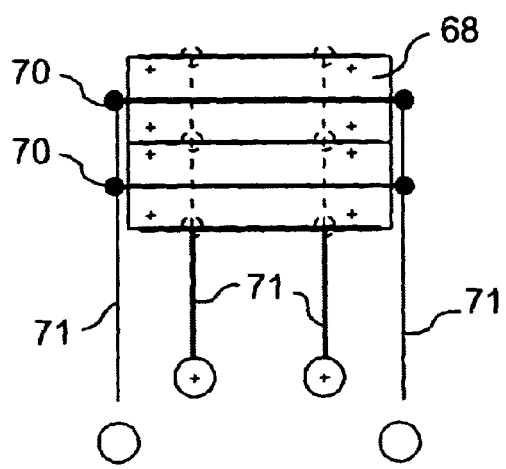
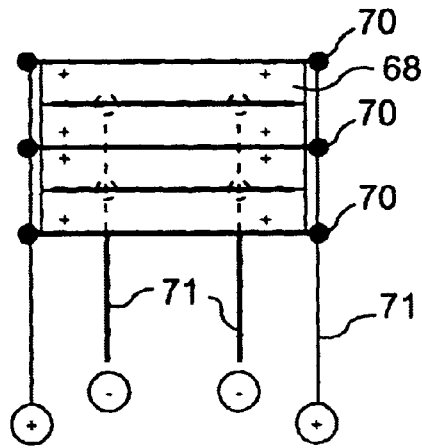
FIG. 11(a)      FIG. 11(b)
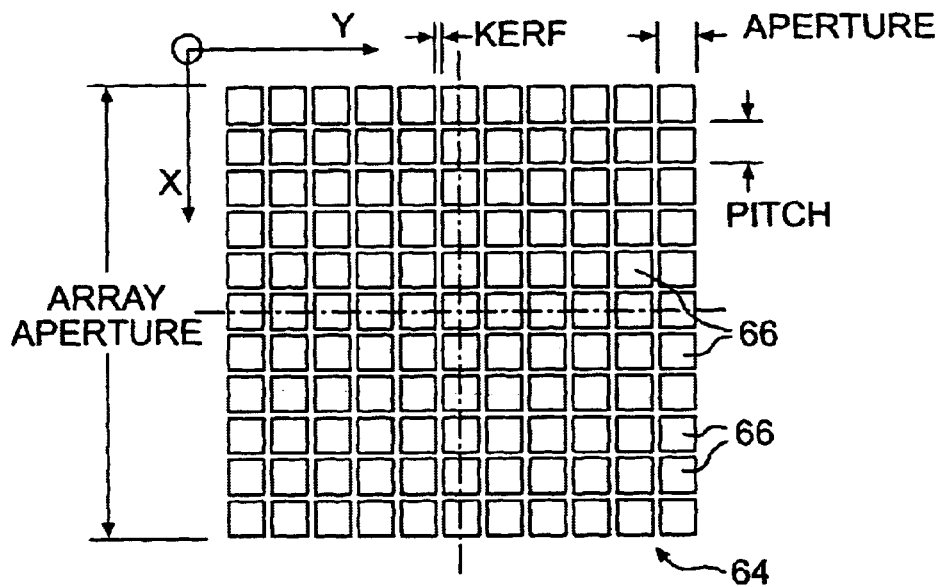
FIG. 12

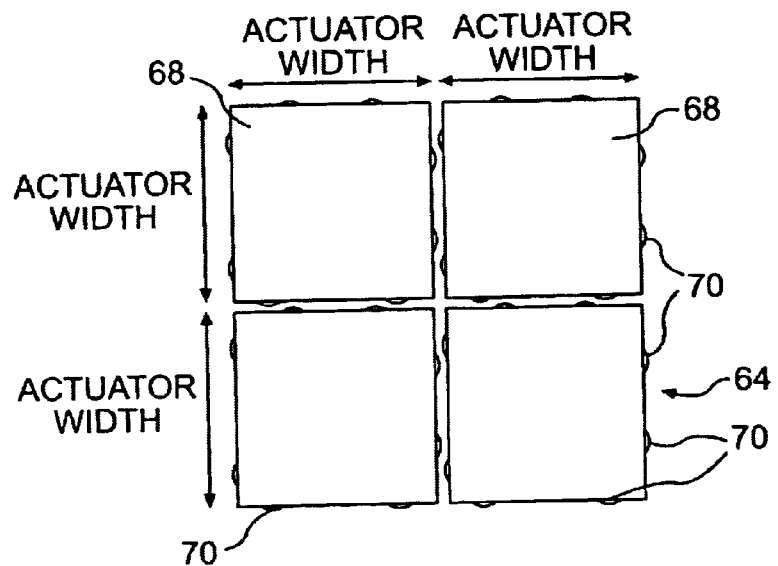
FIG. 13
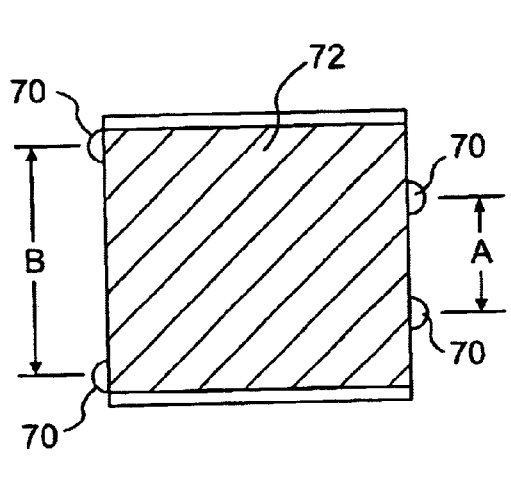 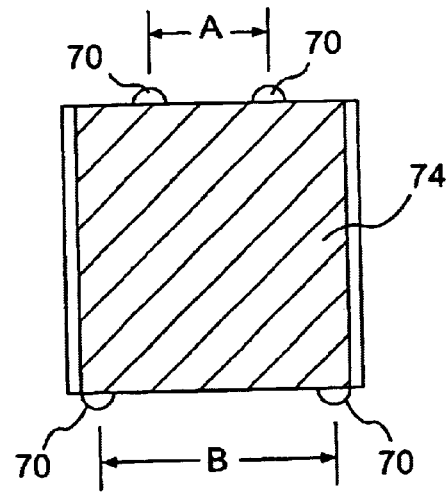
FIG. 14(a)     FIG. 14(b)

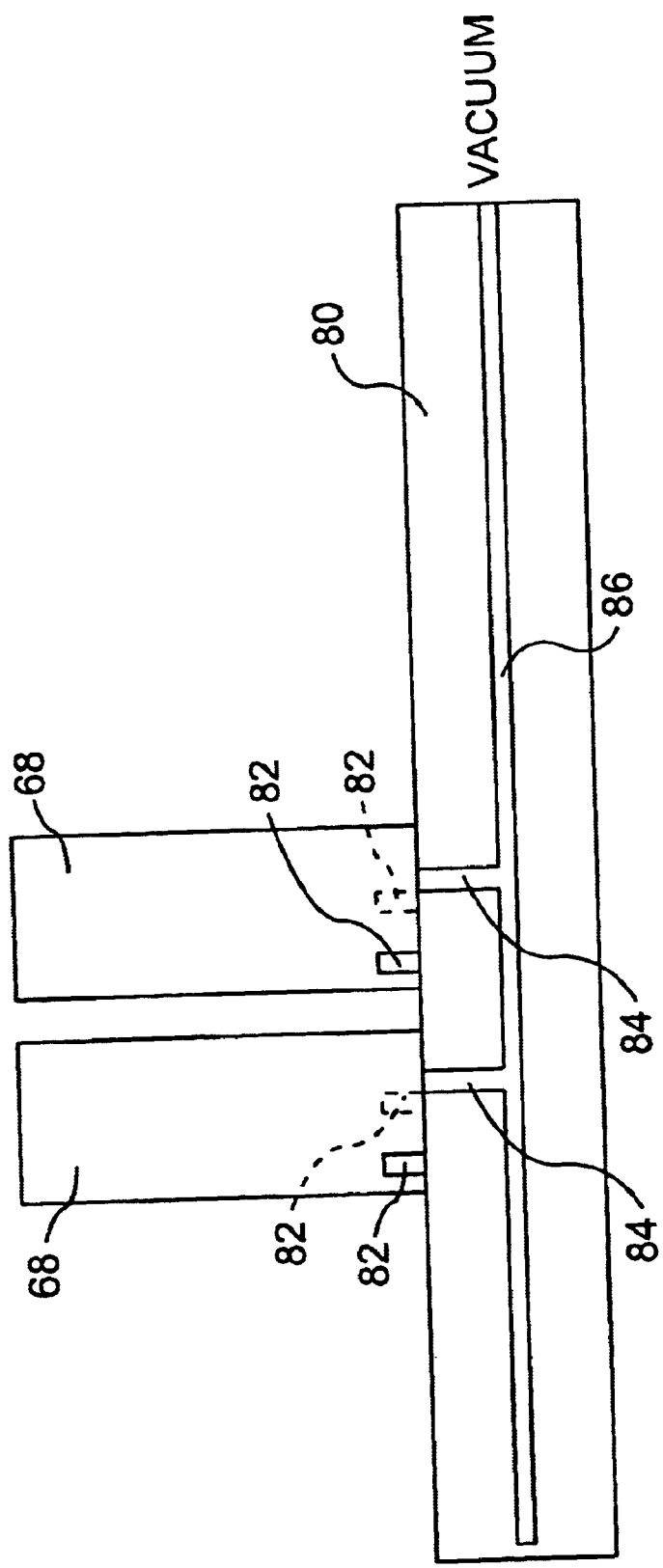

STACK BASED MULTIDIMENSIONAL ULTRASONIC TRANSDUCER ARRAY

BACKGROUND OF THE INVENTION

1. Field of the Invention

The present invention relates to ultrasonic imaging transducer arrays designed for medical applications, and, more particularly, to transducer arrays based on multilayer piezoelectric structures which provide improvements in the electrical and acoustic behavior of the transducer arrays and to methods of making such arrays.

2. Description of the Related Art

Imaging human organs by ultrasound is an essential modality in most medical specialties and particularly in the fields of obstetrics, radiology and cardiology. The ultrasound or ultrasonic transducer is the limiting element that determines the quality factor of the diagnostic imaging. Several types of ultrasound transducers exist, ranging from sector moving single elements, to electronic linear arrays and to multidimensional arrays. The latter is the most sophisticated device currently available for imaging applications.

Conventionally, linear arrays comprise elementary transducers arranged along a single axis, while multidimensional devices comprise elements disposed in orthogonal planes to provide either am expanding lateral focus or crossing B-mode planes useful for rendering 3D images. Additionally, the term "1.5D" array is given to a linear array having transducer rows independently addressable in elevation. This arrangement provides the possibility of producing a better focussed ultrasound beam in the depth direction of examination by switching and synthesizing apertures along this direction. Similarly, the term 2D array or matrix array is usually employed for transducers having elements of square shape uniformly distributed in two orthogonal directions of the front plane. This arrangement permits the transducer device to perfectly synthesize the beam pattern or to correct phase aberrations due to the tissue or acoustic aperture when used in a conventional application. Volumetric or multiplane imaging approaches are only feasible with this type of device if movement of the transducer device during the image acquiring process is not desired.

Geometric specifications for linear phased arrays require that each elementary transducer exhibit an angular response of +/-45° which results in an acoustic aperture of about one wavelength for each individual transducer. This requirement enables the array to limit the emergence of grating and side lobes that introduce artifacts into the image. This requirement must be observed for any imaging array device including those designed for 1.5 and 2D use. Because the frequencies of transducer are usually in the range of 3 to 10 MHz, the elementary transducer aperture inherently varies from 0.150 mm to 0.50 mm in width in order to satisfy the acoustic radiation requirements. These dimensions pose severe fabrication difficulties in achieving repeatable elements and interconnections.

Other difficulties that affect the design of such narrow band transducers concern the surface of the transducer element forming the device and the mismatch in electrical impedance created when compared to conventional electric circuits. Inherently, low sensitivity and an oscillating or undamped impulse response can be observed with such transducer elements. This drawback is partially overcome in a linear phased array by increasing the elevation aperture of the array in order to expand the surface area of the transducer element. Unfortunately, this solution is not suitable for 1.5D and 2D array devices where the surface area of each element is completely bounded or predetermined. In this regard, the worst case is that of the 2D array where square shaped element transducers are required.

Considering this point further, as discussed above, considering this point further, a critical problem associated with 2D array construction concerns the electrical and capacitive characteristics of the transducer elements. In this regard, it is noted that the capacitance of a piezoelectric or dielectric element is a function of the dielectric constant, the surface area and the thickness of the material. Specifically, the capacitance is calculated based on the relation:

$$C = \frac{\varepsilon_r \times S}{e},$$

where $\varepsilon_r$ represents the relative dielectric constant of the piezoelectric material, S the surface area and e the thickness of element. The capacitance of a transducer element directly governs reflection of the incident energy and this effect is emphasized when the capacitance value is substantially lower than that of the transmission line. Furthermore, a lower transducer capacitance also tends to lower the energy storage capability of the transducer device so that sensitivity is significantly affected.

The recent development of high dielectric constant piezoelectric materials such as relaxor based ceramics or single crystals has resulted in high density linear phased arrays which outperform conventional transducers made of standard ceramics. These new transducer constructions employ piezoelectric materials having a relative dielectric constant as high as 5000 in order to minimize capacitance loss. However, this approach to optimizing transducer devices is only obtained at the expense of a severe limitation on the operating temperature to avoid risk of depolarization or premature aging of the device.

Returning to a consideration of transducer arrays of 1.5D and 2D configurations, the excessively small surface area of the transducer element undermines the advantages associated with the materials described above, so that difficulties are encountered by engineers in the development and manufacture of such devices. In order to overcome the capacitance mismatch problem, attempts have been made to integrate active impedance matching into the device and to provide built-in driving circuitry connected to each transducer, with some relative success. However, the heating of such components results in a rapid rise in the temperature of the transducer and therefore results in excess current regulation for medical devices. Other attempts involve the use of multilayer structures in 2D arrays wherein sophisticated manufacturing techniques have been implemented, such as micro via methods and screen printing processes. However, such a fabrication process is not suitable, in practice, for low volume production and thus this technology for transducer fabrication still remains in the laboratory prototype stage. Further, the acoustic performance is yet to be confirmed.

Turning now to 1.5D arrays wherein the obstacles encountered are less important than for 2D arrays, the main problem regarding this kind of transducer is the variation in the surface of the transducer element when viewed in a common elevation plane. The transducer elements, which are conventionally disposed in the azimuth direction are further arranged in parallel rows that are organized in concentric manner along the elevation plane. Indeed, such rows have the elevation dimension thereof shifted in a manner so as to exhibit a wider aperture at the central area of the transducer array and provide the narrowest aperture at the edge of transducer.

In order to optimize the geometric aperture of a 1.5D array, a Fresnel synthetic aperture may be advantageously provided in the elevation plane. However, this approach presupposes that the transducer is equipped with row apertures downshifted or varied according to a specific law of progression designed to reduce the side lobes emanating from such a synthetic aperture construction. Advantages relating to the provision of an elevation synthetic aperture for an imaging linear array include the ability to modify the focal distance in the plane of space in contrast to conventional devices which only provide a fixed focus. However, in the construction of such devices a major obstacle is encountered which has not been fully addressed in the prior art. This obstacle concerns the electrical impedance variation between a transducer element belonging to a given row and that of another row. This varying impedance characteristic leads unavoidably to a dramatic decrease in the sensitivity and bandwidth of apertures having a smaller elevation dimension, thus producing focus aberration. Reported systems have attempted to overcome this problem by implementing a predetermined gain compensation for the corresponding driving circuitry, but this approach impacts on the price of the apparatus and encumbers the construction thereof because these add-on circuits must be located on the vicinity of the transducers in order to be efficient.

With regard to 2D arrays, there have been reported at least two principal construction technologies, viz., collective on-chip construction and conventional acoustic construction. Each of these technologies suffers specific advantages and weaknesses which are summarized below.

Conventional acoustic transducer construction is perhaps the most elementary technique employed for obtaining 2D arrays, in that each transducer element of the array is individually considered and built, and the resultant assembly of a plurality of transducer elements forms the array. The approach is based on the provision of a piezoelectric member mounted on a backing block which serves to maintain the geometry of array and to provide elimination of backward acoustic reflections. The front face of the devices is commonly loaded by matching layers so as to optimize energy propagation in the medium under investigation. This technology offers interesting transducer performance in linear array constructions but has proven to be subject to very difficult fabrication problems when applied to 2D arrays because of problems associated with making electrical connections and the overall complexity of assembly of the construction.

Another technique of forming 2D transducer arrays concerns the use of piezoelectric elements performed on silicon or insulated substrates. Such a backward insulated substrate facilitates providing electrical connections for the transducer elements and this lowers the fabrication costs. However, the high acoustic impedance of such substrates and the low acoustic attenuation coefficient of the material used make the resultant device subject to strong artifacts from echo signals due to reverberations in the thickness of the substrate. Regarding the large number of elements to be connected in 2D arrays, although this results in certain weaknesses in acoustic response, investigations into collective fabrication methods for obtaining 2D array have been carried out by a number of transducer manufacturers because of the expected potential reduction in fabrication cost.

The prior art includes several fabrication methods for multidimensional arrays including the electrical connection method for 2D arrays disclosed in U.S. Pat. No. 5,311,095 to Poulin et al. This method provides for a multi-layer ceramic connector as well as a mismatching layer for extending the electrodes of the array elements to the connection cables. The transducer is made from standard piezoelectric material and the method enables the transducer manufacturing process to be carried out by using a simple bonding operation. However, the thickness of the mismatching layer and the MLC favor the occurrence of reverberations in the pulse response of the transducer. Furthermore, the surface of each transducer element is so small that strong electrical reflections are induced which appear as oscillations in transducer response due to impedance mismatching.

One prior art reference which addresses the problems of impedance mismatch in linear arrays is U.S. Pat. No. 4,958,327 to Saito wherein a N×layer piezoelectric member is used in linear transducer arrays. However, the technique for providing connections between the piezoelectric layers is limited to lateral short circuits and has provide to be inadequate for 2D transducer array fabrication.

A further technique is described in U.S. Pat. No. 5,381,385 to Greenstein et al which discloses a method for obtaining multilayer piezoelectric structures for use in matrix transducer arrays. Green ceramic layers are provided with holes performed in the surface thereof. Conductive vias are provided through these holes. Thus, when several layers of green ceramic are assembled together to form a multilayer structure, and the piezoelectric layers are connected in parallel, the capacitance is increased by a factor of the square of the number of layers, resulting in advantages which will be evident to one skilled in the art. However, this connection approach requires high volume fabrication in order to be cost effective as well as a high degree of precision in positioning the assembly of layers. Moreover, a via obtained by mechanical drilling or laser machining is subject to peripheral depoling of the surrounding material which may affect transducer performance and the homogeneity of the surface of the transducer.

In U.S. Pat. No. 5,548,564 to Smith et al, there is described a multilayer ceramic 2D array transducer wherein the piezoelectric layers are preferably assembled in parallel in an arrangement which is said to provide enhanced capacitance and impedance characteristics to the array. The method described can also be extended to composite material. However, as discussed, the feasibility of efficiently making such a transducer array depends on accurate alignment of the different layers of piezoelectric and further, the drilling of microholes remains an uncertain approach regarding reliability and will also affect the homogeneity of the array, and homogeneity is an essential criteria for acoustic devices.

U.S. Pat. No. 5,825,119 to Ossmann et al describes a multilayer structure-based transducer array for harmonic imaging wherein several operating modes are provided. The Ossmann et al patent is concerned with providing a transducing system having the ability to operate at two selected frequencies in order to transmit ultrasonic waves at one frequency and to receive the echoes from the structure under test at the other frequency. The method for driving the multilayer transducers is described in connection with embodiments including diode circuits or transistors or varistors or Zener diodes. This description is limited to double layer devices which are well adapted to harmonic imaging and there is no description of the use of this approach in 2D array constructions and the connection problem associated with such constructions has not been addressed.

SUMMARY OF THE INVENTION

In accordance with the present invention, methods are provided for manufacturing 1.5D and 2D ultrasonic array transducers which overcome the various drawbacks and disadvantages mentioned above. The use of piezoelectric multilayer structures as vibrators enables the resultant transducer to satisfy stringent requirements, including those concerning the capacitance characteristics and impedance homogeneity of the transducer. According to a first aspect of the invention, there is provided a novel method of making 1.5D transducer arrays wherein transducer configurations are produced which have shifted elevation apertures from the center to the edge of the array, and wherein the method produces uniformity of transducer capacitance independently of location in the elevation plane of the array. A further aspect of the invention concerns a method of connecting and using standard multilayer actuators to build high performance, cost effective 2D transducer arrays. The method enables manufacturing of superior 2D transducer arrays which possess electrical characteristics comparable to those of conventional linear arrays.

Generally speaking, the present invention employs multilayer piezoelectric fabrication technology to produce nD ultrasonic transducer arrays (e.g., 1.5D and 2D transducers) while avoiding the above-mentioned problems and limitations inherent in this type of device. Novel manufacturing and interconnection methods are provided which produce multi-dimensional transducer arrays useful in imaging or NDT applications. The methods of the invention simplify the manufacturing process and reduce the time necessary for fabrication of the transducer arrays. Moreover, reliability is greatly improved and new transducer configurations can be made as well.

According to another aspect of the invention, a 1.5D linear transducer array is provided in which impedance compensation is provided between the elemental transducer forming the array. Preferably, this impedance compensation is provided by varying the number of layers provided in each row of the elemental transducers so as to make feasible tuning of the impedance parameter.

Yet another aspect of the invention concerns the provision of a 2D transducer array or matrix transducer array wherein elemental transducers are produced by dicing a conventional multilayer actuator to form equal sized elements (pillars) which are embedded in a polymer matrix. Alignment of the individual pillars is provided by microholes which are performed on the surface of the multilayer actuators and which are removed with the dicing of the pillars.

Further features and advantages of the present invention will be set forth in, or apparent from, the detailed description of preferred embodiments thereof which follows.

BRIEF DESCRIPTION OF THE DRAWINGS

FIG. 5 is a side elevational view of a stacked piezoelectric transducer;

FIG. 6 is a perspective view of the transducer of FIG. 5;

FIGS. 11(a) and 11(b) are respective Z-X and Z-Y views of a multilayer ceramic device in accordance with a second aspect of the invention showing the electrical connection therefor;

FIG. 12 is a top plan view showing the front face of a matrix transducer array in accordance with the second aspect of the invention, after sub-dicing;

FIG. 13 shows the array of FIG. 12 prior to sub-dicing;

FIGS. 14(a) and 14(b) are views showing the electrical connection to an elemental transducer of the array of FIG. 13;

FIG. 17 is a side elevational view of a positioning tool showing positioned thereon a pair of transducer elements or pillars.

DETAILED DESCRIPTION OF THE PREFERRED EMBODIMENTS

Before considering the first preferred embodiment of the invention, reference is made to FIGS. 1(a) and 1(b), which are described below and which show a prior art 1.5D ultrasonic transducer array. In the current state of the art, the term 1.5D designates a transducer array formed by an arrangement of elements in a first direction (i.e., the azimuthal direction) and another arrangement of elements in a perpendicular direction (the elevation direction). The pitch of the array is uniform along the azimuth and may be variable in different ways in elevation. The purpose of such constructions is to provide the transducer array with the capability of better focusing in the elevation plane, while the azimuth plane is controlled by electronic phase delays, as commonly employed in linear array driving circuits. As indicated above, 1.5D transducer arrays employed in a radiology modality are capable of providing important improvements in lateral resolution of the image so that the diagnostic image has better contrast and more definition. However, in the actual industrial fabrication of 1.5D transducer arrays, several important technical problems must be overcome including the large number of addressing elements that must be connected and, more critically, the variation in electrical impedance from element to element of different rows of the array.

Figure 1A:
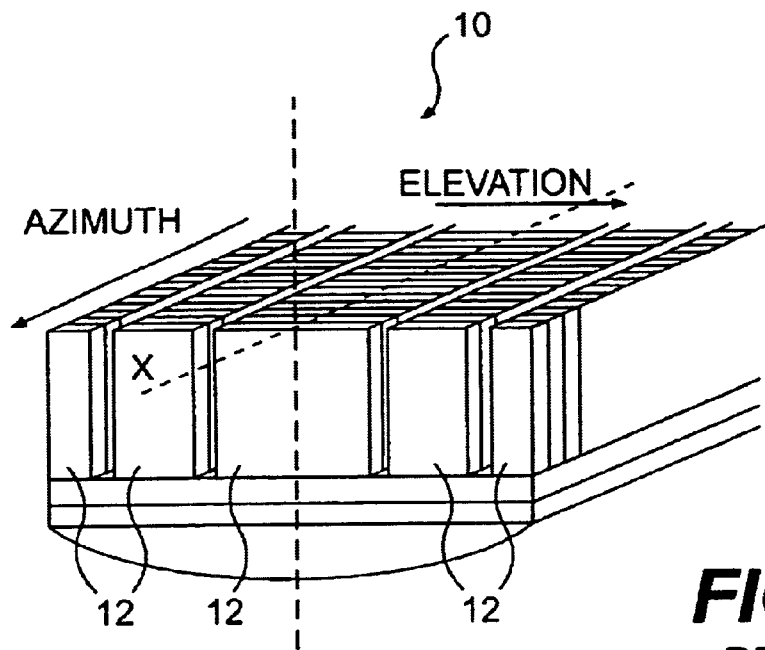
FIGS. 1(a) and 1(b) are a perspective view and a top plane view, respectively, of a prior art 1.5D ultrasonic transducer array.
Figure 1B:
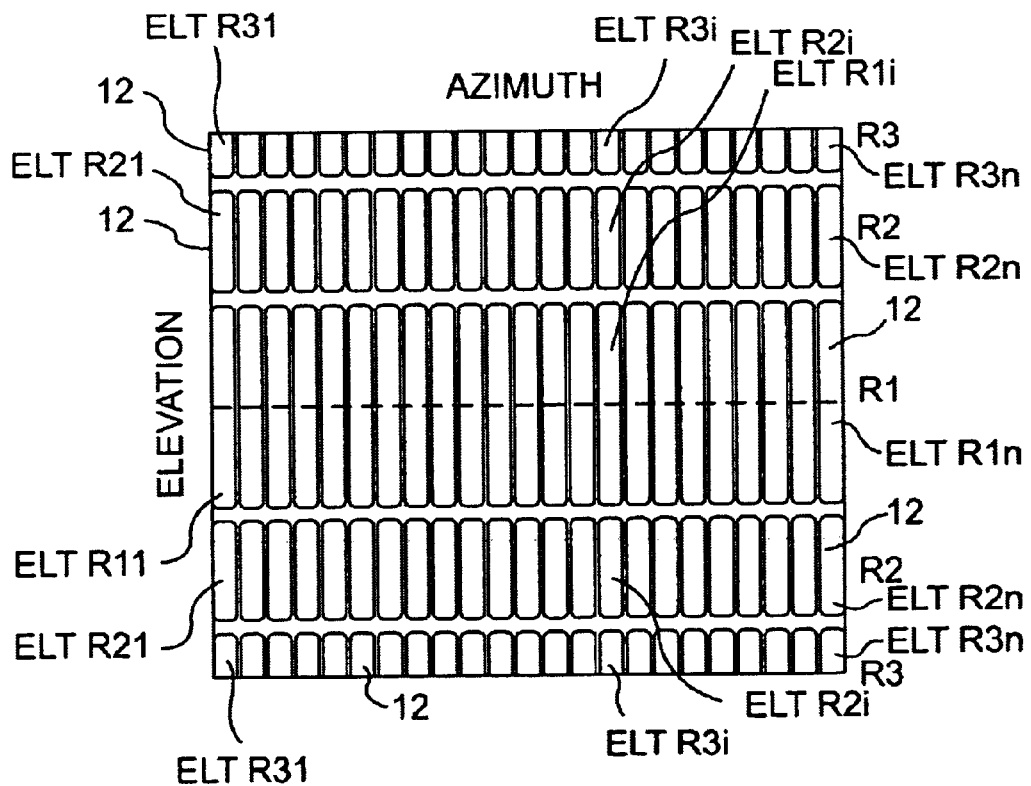
Figure 2:
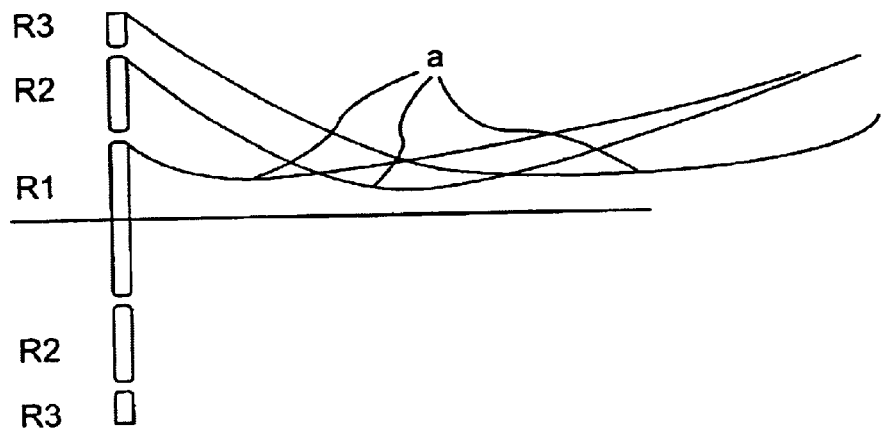
FIG. 2 is a graph showing acoustic apertures for different connections between the rows of FIGS. 1(a) and 1(b)

Referring specifically to FIGS. 1(a) and 1(b), there is shown a transducer array, generally denoted 10, arranged in a 1.5D manner according to the prior art. For simplicity a 3-row aperture transducer array is depicted in FIGS. 1(a) and 1(b), but as will be understood by those skilled in the art, this is merely exemplary and the limiting factor for number of rows basically depends on the capability of system to control the corresponding number of transducer elements. The scanning image is formed by switching apertures along the azimuth direction and transverse focus is obtained by controlling the element or row apertures, denoted 12, which are aligned in elevation. In a first mode of operation, the transducer can be driven with only the central row R1 activated so as to exhibit a narrowed transverse aperture. This mode, which is illustrated in FIG. 2 wherein the various apertures are denoted a, is of use in imaging a proximal zone of interest or superficial objects. However, this narrowed transverse aperture may easily be expanded by connecting in parallel, elements located in the neighboring rows, viz., elements R2 and R3 in the example under consideration. It will be noted that in elevation, elements belonging to rows which are designated as having the same rank (R) are to be connected in parallel to form a sub-acoustic aperture. In the illustrative example, the row R1 is positioned as the center of the elevational height and the others rows of elements R2 and R3 are arranged so as to be symmetric with the central row. Therefore, expanding of this type of aperture will have no impact on the direction of the acoustic path.

This method of modifying the transverse aperture of transducer results in a dynamic expansion of the focal point as well as in an improvement in the lateral resolution of the device along the forefront axis. In order to limit the appearance of artifacts due to the aperture sampling effect, the rows are decreased in height toward the edges, as illustrated in FIG. 1(b).

A second mode of controlling transverse aperture of 1.5D transducer arrays implements phase shifting between rows to shape the aperture so that steering or dynamic focusing of the acoustic pattern is available. This ability greatly improves the quality of the images obtained. Furthermore, steering the acoustic path will enable system to reduce structural "speckle noise" by comparing information from two adjacent scanning lines. The results of dynamic focusing are very simply shown in FIG. 2, wherein the rows of FIG. 1(b) are indicated at R1, R2, R3 and, as indicated above, the three curves denoted b represent different acoustic patterns obtained with the corresponding elevation apertures.

Figure 3:
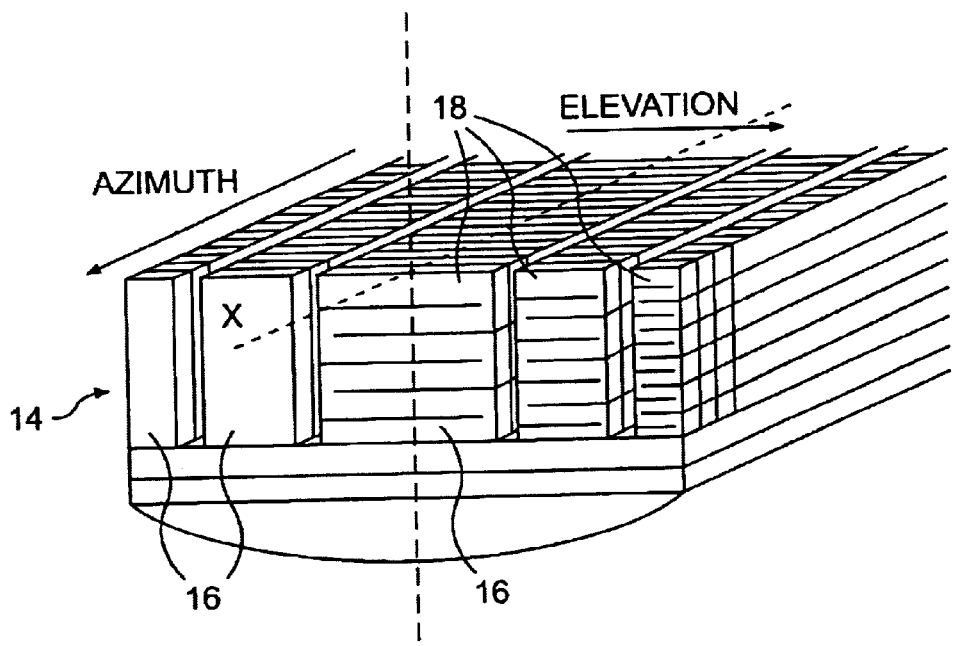
FIG. 3 is a perspective view of an ultrasonic transducer array in accordance with a first embodiment of the invention.

Referring to FIG. 3, a 1.5D stacked transducer array in accordance with one preferred embodiment of the invention is shown. The piezoelectric member, which is generally denoted 14, is composed of a plurality of multilayer rows 16 arranged in the elevation plane. Each row 16 is of a stacked construction wherein the final thickness is determined by adding a given number of piezoelectric sub-layers 18 each having an identical thickness. As described above, the electrical impedance of each transducer is governed by the surface and the number of sub-layers thereof. Because the surface of the transducer array varies from row to row, and because the resonant frequency of the array should be maintained constant, the number of piezoelectric sub-layers 18 is made to vary according to the elevation of the row in order to compensate for differences in impedance. This approach limits the impact on the impulse response of the transducers. Although FIG. 3 shows a transducer array comprising the three rows of transducers, the simplified illustration is for purposes of clarity and the invention is obviously not limited to the exemplary embodiment illustrated.

Figure 4B:
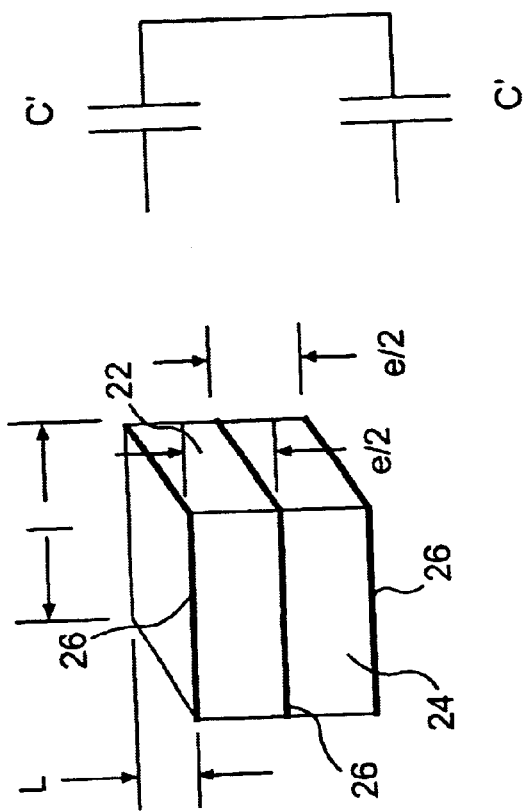
FIGS. 4(a) and 4(b) are perspective views of two different transducer constructions used in explanation of the principles of the stacked piezoelectric concept.
Figure 4A:
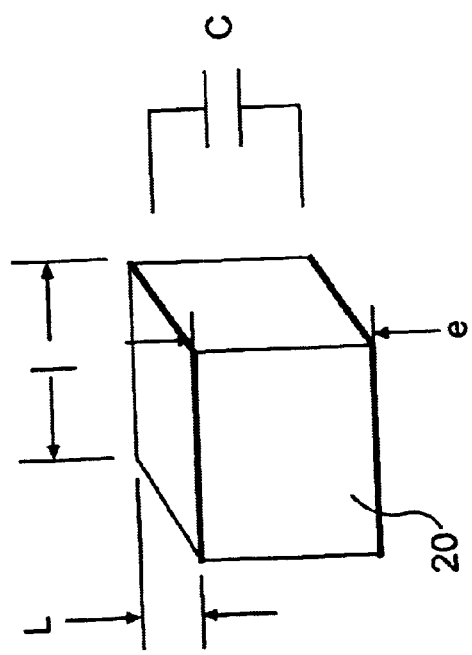

Referring to the FIGS. 4(a) and 4(b), these figures illustrated the principles of the stacked piezoelectric concept in a manner that is believed to be easily understandable by one skilled in the art. FIG. 4(a) shows a single piezoelectric member 20 geometrically defined by its dimensions, denoted L, I and e. The capacitance C of this member is given by the formula $C=(E\times S)/e$, where E is the relative dielectric constant, S is the surface area of the associated capacitor and e represents the distance separating opposed electrodes.

In FIG. 4(b), a second piezoelectric member having equivalent external dimensions is provided in a stacked form, the stack being composed of two layers of piezoelectric 22 and 24 having each of a thickness corresponding to one half of that the piezoelectric member 20 shown in FIG. 4(a). Electrodes 26 are deposited on each of the main faces of the sub-layers 22 and 24 so the resultant stack can be controlled either in series or in parallel depending on the transducer specifications. In the present embodiment, sub-layers 22 and 24 are driven in parallel, meaning that the polarities are reversed and equivalent capacitance enhancement is maximized. In this regard, the equivalent capacitance, $C_{equiv}=4(E\times S)/e=4C$, and the equivalent electrical circuit for each piezoelectric element or member is illustrated at the right hand side of FIG. 2(b). This demonstrates the advantage of stacking a plurality of sub-layers provided that the polarities are reversed to obtain the parallel connection of the sub-capacitances. Again, for simplicity of understanding, FIG. 4(b) shows a stacked arrangement that only comprises two sub-layers, but it will, of course, be understood that however the number of sub-layers is not a limiting factor and will be determined according to the actual capacitance requirements.

An important aspect of the invention concerns an improved method manufacturing which involves the assembly of a plurality of single blocks of a multilayer piezoelectric actuator (MLPA) to form the final 1.5D transducer array. A cross-sectional view of MLPA is shown in FIG. 5 where inter-digital electrodes 28 and 30 surround layers of piezoelectric 32. The MLPA can be selected from standard multilayer piezoelectric products (e.g., Morgan Matroc, APC or Ferroperm) or can be custom designed by stacking ceramic or composites or single crystals.

MLPAs are preferably constructed with a length dimension corresponding to the azimuth of the array, as shown in FIG. 6, with each MLPA having a specific width corresponding to the row aperture. The electrodes of MLPA are preferably connected to the system in the manner shown in FIG. 6, so that, as illustrated, the electrodes 30 of a first group with externally located elements are preferably connected to the system ground while the electrodes 28 of the opposite group are connected to a driving circuit indicated at 34.

Because the impedance of am MLPA varies as the square of the number of piezoelectric layers, perfect adjustment of the impedance value of the transducer may be difficult to achieve. However, a variation less than 30% of the nominal value would be considered as acceptable and will not impact significantly the performance of the transducer. The impedance ratio within a 1.5D transducer can be a factor of three between the central element and the first adjacent element, and may be as high as a factor of 10 for the outermost elements. Once the number of sub-layers for each row is determined, the MLPA is then diced in individual portions so as to form the array of elements. This dicing will also determine the pitch of the array.

Figure 7:
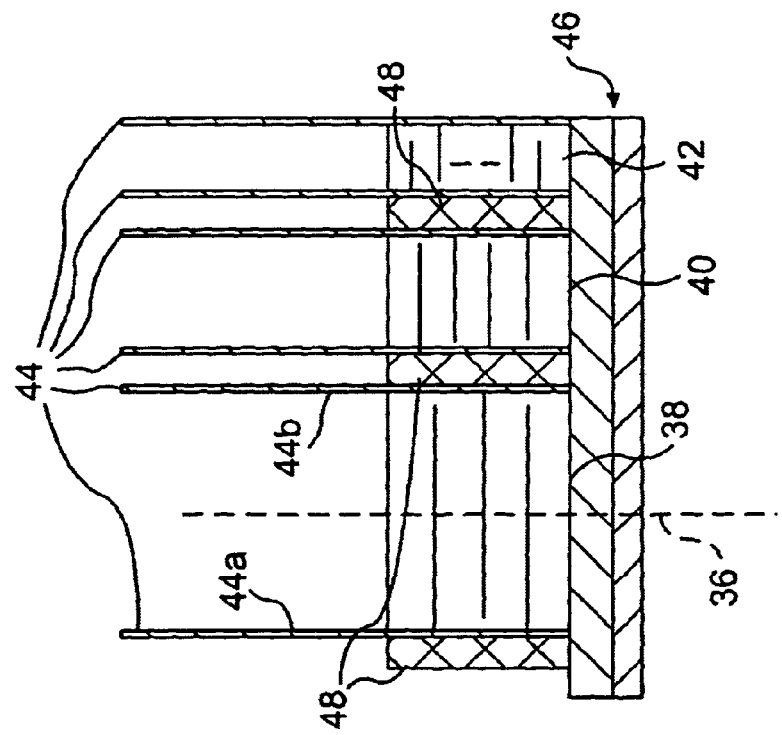
FIG. 7 is a cross-sectional view of a transducer array in accordance with a further embodiment of the invention showing one stage in the construction thereof.

Referring to FIG. 7, there is shown in more detail a 1.5D multilayer array transducer. FIG. 7 shows the array in an elevational sectional view in the axis of symmetry as indicated at 36. In FIG. 7, one half of the elevation is shown with exception of the central row 38 which is depicted in its totality. Each row 38, 40 and 42 is provided with its corresponding flex connection circuits 44 bonded to the lateral side surface thereof as shown.

The technique for assembling the flex circuits to the MLPA device can be chosen among a number of known techniques including non-conductive bonding, diffusion bonding or ultrasonic welding or any other suitable bonding technique. The flex circuit 44 is provided with conductive traces (not shown) printed on the surface thereof facing the MLPA. The pitch and width of the traces are selected based on the pitch of the array to be manufactured. In general, traces are designed to have the same pitch than that of the array for a single flex assembly and to have twice the array pitch for a dual flex configuration. In the latter case, the MLPA is laterally sandwiched by the flex circuits 44 and trace patterns are shifted to obtain an inter-digital arrangement wherein a first flex circuit, denoted 44a, is aligned with and connected to the first element of array and with the other odd numbered following elements, while a second flex circuit, denoted 44b, is connected to the second element of the array and the other even numbered following elements of the array. Whatever the technology employed for assembling the flex circuit 44, it is preferable to have the same flex circuit assembly method for all rows comprising the transducer array.

A second factor that governs the number of flex circuits required is the cable-flex circuit interface. In this regard, in order to determine the most suitable method for a particular transducer array apparatus, considerations such as fabrication cost and the reliability of the resultant product must be taken into account.

Once the MLPAs are provided with their flex circuits, alignment of the MLPAs is then required on a matching layer set, indicated at 46, before the bonding operation is performed. As will be understood by those familiar with this art, a set of matching layers is conventionally a part of a standard transducer array. The bonding operation must be done with care to ensure perfect alignment of the MLPAs in the azimuth and elevation planes, and preferably a specific tool is used in guiding this operation. A suitable adhesive or glue, such as Epo 301 from Epotech Corp., is then laid out on the surfaces to assemble flex circuits 44 and MLPAs 38, 40 and 42. Pressure and heat are preferably applied during curing period. Further, it is important to spread the pressure uniformly on the bonding surface so as to ensure good electrical contact between the electrodes of MLPAs and the flex trace pattern. Therefore, the preferred method is to provide an elastomeric layer between the pressure tool and the surfaces to be assembled. A material such as Santoprene 281-55 from Advanced Elastomer Systems (USA) is well suited to the application although other elastomers can, of course, be used as well. The flexibility of the elastomer will accommodate misalignment or surface defects in the components. Otherwise, the bonding resins used may be readily selected among a number of candidates, including epoxy, polyurethane or any suitable available glue, even those requiring UV curing.

As indicated above, the use of the previously mentioned matching layer set 46 is well known in the art and the set is chosen based upon physical criteria such as acoustic impedance (this impedance should be between that of the MLPAs and that of the propagation medium), sound velocity and attenuation coefficients. In common practice, a double layer matching set is preferably provided to enhance the performance of the transducer array. Usually, the physical properties of the matching layers are custom designed so as to maximize the energy transfer to the human body. For this purpose, mineral or metal particle filled polymers and unfilled polymers are ideal candidates for matching the acoustic energy in medical imaging applications.

The assembly of rows to form the final array requires particular attention to the acoustic coupling between the rows of the array. To reduce lateral cross coupling between rows, acoustical absorbing sheets 48 are disposed at the interface between the rows along the azimuth. Sheets 48 are, for example, made from polyurethane or polybutadiene with acoustical diffusing embedded particles. The thickness of the sheets does not need to exceed about 0.5 to 1 mm in order not to disturb the forefront acoustic path. In another embodiment, the absorbing sheets can have thicknesses which vary from the central row to the outermost rows in order to improve the acoustic radiation pattern in this plane.

Figure 8:
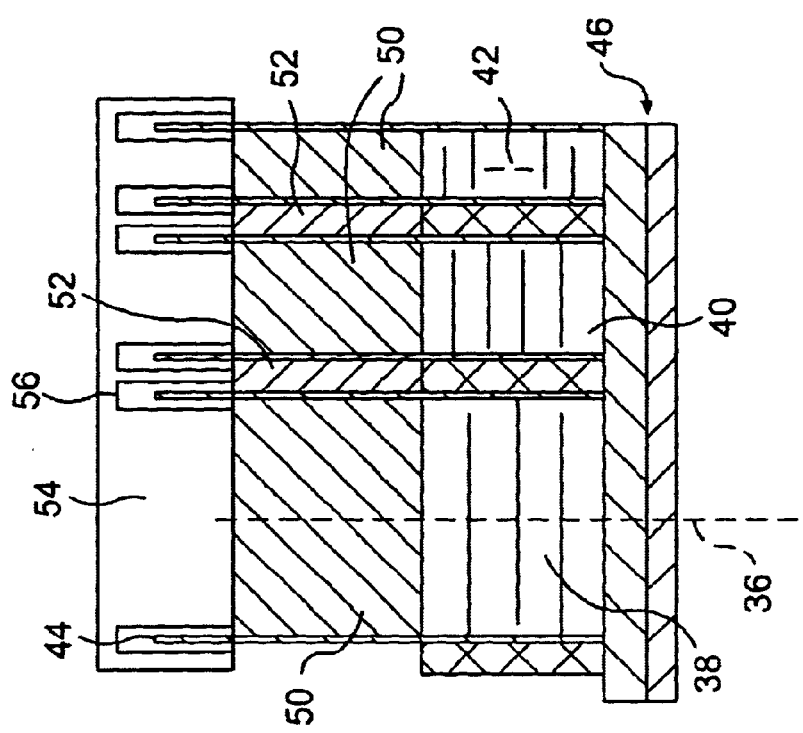
FIG. 8 is a view similar to that of FIG. 7 showing a later stage in the construction thereof.

As will be understood by those skilled in this art, a piezoelectric transducer generates ultrasonic waves on the two opposite faces thereof when excited by electrical pulse. However, wave propagation on only one side is of interest. Therefore, acoustic waves emanating from the other face must then be eliminated so as to avoid artifacts. FIG. 8 shows a series of backing members 50 disposed on the rear face of the MPLAs 38, 40 and 42 of the transducer to dissipate reflection energy from this side. The role of the backing member 50 is also to acoustically dampen the rear face of the transducer to shorten the impulse response. In the embodiment of FIG. 8, the backing members 50 have dimensions according to those of the corresponding rows. The thickness is governed by the attenuation factor of material. Typically, a 70 dB round trip attenuation of the emitting signal is acceptable for imaging applications. However, a 80 dB round trip attenuation is preferred for high quality imaging.

The backing composition for backing member 50 can be one chosen from a large number of different polymers and mixing particles available on the market. However, the preferred backing composition for an ultrasonic array transducer is that obtained by mixing adjustable proportions of plastic microbubbles, mineral particles and metal oxide particles into flexible resin, such as Stycast 1264 made by the Stycast Corp (USA). Such a composition has the advantage of offering a high acoustic impedance and a large attenuation factor. Further, the flexibility provided by the resin enables the backing member to be implemented with Lamb wave attenuation so as to improve the inter-element cross coupling coefficient.

Each backing member 50 is disposed on its respective MLPA as shown in FIG. 8, and flex circuits are then affixed to the lateral faces of the backing member. The remaining spaces 52 are preferably filled with soft resin to maintain in place the flex circuits.

Because separate backing members 50 are provided for each MLPA, a stiffener 54 is disposed on the rear face of the backing members 50 to provide additional stiffness to the apparatus. Preferably, stiffener 54 is made of a thermally conductive material such as aluminum or a resin filled with aluminum oxide particles. Moreover, stiffener 54 is preferably provided with grooves 56 where are aligned with the outwardly extending portions of the flex circuits 44 so the flex circuits 44 are directed laterally out of the transducer.

At the stage illustrated in FIG. 8, the transducer array is almost complete, although flex circuits 44 still need to be connected to the coaxial cable or multiplex modules (not shown) prior to connection to the mainframe. This activity can be carried out by appropriately fine pitch connectors such as those supplied by Molex Corp, USA.

Figure 9:
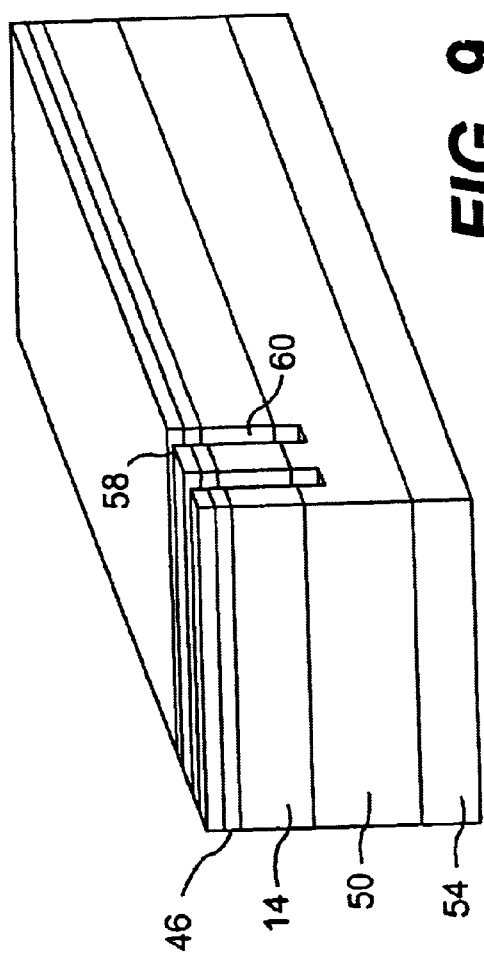
FIG. 9 is a perspective view of a transducer portion of the transducer array of FIGS. 7 and 8.

FIG. 9 shows the transducer array 14 turned upside down and grooves 58 provided in the elevation direction and along the azimuth axis so as to split the device 14 into the elementary transducers. It will be apparent that grooves 58 must be perfectly aligned on the trace patterns of the flex circuit if no separating or shunting element is desired. In the conventional technique of array fabrication, cutting or dicing is performed to a sufficient depth to make the elementary transducers independent of one another and this contributes to an improvement in the cross-coupling characteristics. In the present invention, a complete dicing of the MLPA devices is required to obtain the desired effect of the multilayer structure. Cutting the backing layer 50 may provide the further benefit of reduced Rayleigh wave propagation which also leads to lower inter-element cross coupling. The grooves 58 so obtained significantly affect the transducer behavior. In this regard, the region surrounding grooves 58 may be the site of spurious vibrations responsible for cross-coupling in the array. Therefore, the grooves 58 should then be filled with attenuating material 60, e.g., suitable resins, in order to efficiently combat the cross-coupling modes. The preferred candidates for the material 60 used for filling the grooves 58 are Ecogel 1256 from Epotechny US, or polybutadiene, from Atochem or silicon rubbers. Air filled grooves can also be achieved by attaching a thin film (not shown) of Mylar or polyamide on the surface of the transducer.

Figure 10:
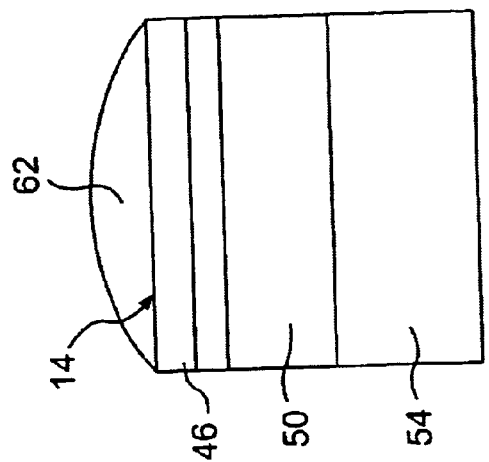
FIG. 10 is a side elevational view of the transducer portion of FIG. 9 showing a further step in the construction thereof.

Because the 1.5D array is larger than conventional 1D array in elevation, as shown in FIG. 10, the transverse focus is preferably performed by a convex focusing (e.g., silicon) lens 62 in order to improve the contact surface with the transducer body. It is noted that the convex shape of the silicon lens 62 is obtained by choosing a lens material having sound velocity lower than that of sound in the body being examined.

As mentioned above, the stacked transducers described previously are assembled to each other with reverse polarity and thus it is convenient and efficient to provide the device with an additional shield or screen (not shown) disposed over the matching layer surface. This shield or screen can be provided by sputtering a metal (e.g., gold, copper, or aluminum etc) over the external surface of the transducer. Other suitable shielding techniques include the use of a copper foil or metallized polyamide film disposed between the matching layer and the lens. Thereafter, the shield is then connected to the ground plane of the mainframe unit so as to provide the system with optimal interference protection.

Considering an exemplary non-limiting example by way of explanation, a 1.5D array transducer as described above may have a configuration and dimensions, with three independent rows disposed as shown in the drawings as follows: total elevation height=17 mm; central row (single row)=12 mm; first double row=4 mm (2×2 mm); second double row=1 mm (2×0.5 mm). Surface ratios for the center/first row and first row/second row are, respectively: 3 (12 mm/4 mm) and 12 (12 mm/1 mm). This configuration has the advantage of providing surface ratios close to a factor 4 so that the capacitance of each row of array is approximately double that of its inner neighbor. Therefore, as shown in FIG. 4(*b*), the number of layers for each row must be increased by one every time the row position is shifted toward the edge of array. Accordingly, if n is the number of layers of the central row, then the first row will have n+1 layers and the second row n+2 layers. The above example is believed to clearly show how the 1.5D multilayer transducer array described above can be achieved by assembling MLPA devices as different as 12 mm (×1), 2 mm (×2) and 0.5 mm (×2) having, respectively, a number of layers of equal to n, n+1, and n+2.

In the second preferred embodiment of the invention, multilayer stacked piezoelectric devices are again used to build matrix or 2D arrays. The method of this embodiment is concerned with reducing the fabrication cost and improving the reliability of the apparatus and, in addition, enhancing the electrical properties of the elementary transducer. Each element of array is obtained from dicing of a commercial square multilayer piezoelectric device. New fabrication and assembly methods have been developed in order to facilitate the manufacturing of device. A first aspect of the method of the embodiment concerns the use of a plurality of rectangular section MLC (multilayer ceramic) pillars to form an intermediate matrix that exhibits an elementary pitch which is double that of the final transducer to be produced. A second aspect of the method concerns a method of making electrical connections to MLC pillars and a method for positioning MLC pillars in the matrix transducer. A third aspect of this embodiment concerns a method for obtaining the final transducer elements of the matrix transducer array by dicing the MLC pillars in identical quarters with respect to dimensions and geometrical distribution of the matrix transducer.

The matrix array transducer according to the second preferred embodiment is piezoelectric multilayer based as already described in detail above with respect to the 1.5D transducer. The use of standard multilayer ceramic (MLC) devices manufactured and designed for actuator applications allows the use of low cost implementation MLC technology in producing matrix array imaging transducers. Unlike other methods reported in the literature, there is no requirement for either conductive vias to connect the layers together or for implementation of a thick-film ceramic deposition technique.

Based on the particular characteristics discussed above regarding MLC device construction, as discussed below in connection with FIGS. 11(*a*) and 11(*b*) which are views taken in the Z-X and Z-Y planes, the number of layers comprising an MLC can be significantly increased to compensate the impedance mismatch of a matrix element with regard to the transmission line. According to a common requirement for imaging array transducers, the element width in the steering plan should not exceed the wavelength of the transducer if it is desired to avoid excessive side lobes. In some particular cases, half wavelength elements are even recommended when enhanced deflection of acoustic pattern is required. In the example under consideration, a matrix array transducer according to the preferred embodiment is provided with an element width of one wavelength. However, the method can readily be extended to the half wavelength element configuration with no significant change.

Before considering FIGS. 11(*a*) and 11(*b*) in more detail, reference will be made to FIGS. 12 and 13. FIG. 12 shows the front face of a matrix transducer array 64 with square elementary transducers 66 arranged in the perpendicular direction of the surface shape the array. The transducer elements 66 are separated each other by a kerf (a passive space or groove separating two consecutive transducers) so the pitch of array 64 is defined as the sum of an acoustic aperture and a kerf.

In FIG. 13, which shows array 64 prior to sub-dicing, standard MLC pillars 68 are provided which are selected to have a longitudinal frequency corresponding to the desired transducer frequency. Further, the square dimension of the MLC pillars 68 is chosen to be approximately twice that of the array. For instance, if the array pitch is of 0.5 mm, the MLC dimension will be around 1 (2×0.5)mm. In actual practice, the dimension of the MLC pillars 68 before assembly thereof into the transducer array is determined to be twice the pitch of the array minus one kerf width, to be exact.

In the usual commercial product, MLC pillars, corresponding to pillars 68, are supplied with two main electrical connections located on the opposite vertical sides of device (not shown), one for connecting the even ranked layer electrodes and the other for connecting the odd ranked layer electrodes. However, MLC pillars suitable for the present invention are provided with a dual pair of electrical connection pads 70 shared on each vertical side of device, as is better shown in FIGS. 11(*a*) and 11(*b*). This arrangement or disposition of the electrical connection pads 70 is an important consideration regarding feasibility of the process, and will be discussed in further detail below. Preferably, the ceramic type is one selected from the group including PZT and, particularly, the Navy V type that has a high dielectric constant, $d33$, and electromechanical coupling coefficients. Examples of such ceramics are PZT5H from Morgan Matroc, HD3020 from Motorola, PZ29 from Ferroperm, among others. Further, materials such as piezoelectric single crystals from the family of PZN-Pt or PMN-Pt are also excellent candidates and their intrinsic performance can be even superior to PZT ceramics.

Referring again to FIGS. 11(*a*) and 11(*b*), each MLC pillar 68 is equipped with eight connection pads 70 disposed on the four lateral sides of the pillar 68 as shown. Connecting wires 71 connected to the pads 70 must be disposed according to the showing in FIGS. 14(*a*) and 14(*b*) wherein the locations of solder pads 70 are clearly identified. FIG. 14(*a*) shows an electrode 72 of the MLC pillars at a given level and FIG. 14(*b*) shows its neighbor electrode 74 located just beneath or just above. This feature is one of the most important aspects of pillar preparation.

It is noted that asymmetric position of solder pads 70 on the pillar 68 is defined in manner to minimize risk of an electrical short circuit between contacts from adjacent pillars. Furthermore, wires 71 (shown in FIG. 11) are preferably of flat shape so as to minimize the thickness of solder pads 70. A suitable wire type is copper sheeting with 0.05 mm thickness. Wires 71 located on the same face of a pillar are connected to the same layer electrode so the wires are at the same potential.

As shown in FIGS. 14(*a*) and 14(*b*), there are two pairs of wires separated by a lateral distance A (so-called "pairs A") and two other pairs of wires separated by a lateral distance B ("pairs B"), making a total of eight connection wires as mentioned above. The pairs A are disposed on the adjacent sides of the pillars as are the pairs B. It is noted that the distances A and B are selected to be of a difference in length of at least an amount greater than twice the width of the connection pads.

Methods for soldering the wires 71 can be selected among using solder paste, ultrasonic welding, and parallel gap or non-conductive pressure bonding, among others. Although manual soldering or bonding of the wires is feasible, this technique requires particular skill to perform, and given the number of MLC pillars to be mounted and connected, automatic soldering methods are advantageously used.

Figure 15:
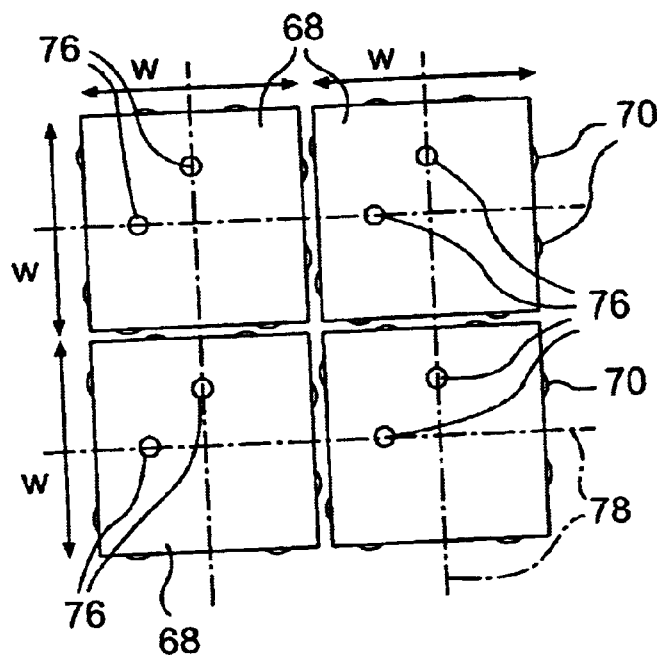
FIG. 15 is a view similar to that of FIG. 13 showing positioning or guiding holes.

The assembly of MLC pillars 68 to form a matrix array requires a particular approach or method. FIG. 15 illustrates the method prior to sub-dicing and shows how the MLC pillars 68 must be arrayed to avoid contact between connection pads 70 of adjacent MLC devices. To enable the MLC pillars 68 to be properly positioned in the array, two positioning holes 76 are provided in the front face of the MLC pillars 68. Positioning holes 76 are preferably obtained by laser drilling or mechanical drilling. Holes 76 are perfectly aligned with the axes 78 of the MLC pillars so the holes 76 will be removed during the sub-dicing operation, as is discussed below and will be evident from FIG. 16 which shows the pillars 68 after sub-dicing.

Turning again to the matrix array assembly operation and referring to FIG. 17, MLC pillars 68 are assembled into a matrix assembling tool or positioning tool 80, which is provided with small pins 82 for guiding the MLC pillars 68 to their final position. It is noted that two pins-hole sets are necessary to prevent movement of the MLC pillar 68. In order to maintain the MLC pillars 68 in place during assembly process, at least one vacuum hole 84 is provided on the surface of the tool 80 in contact with the corresponding MLC 68. The vacuum is supplied through a common vacuum line 86 and the force of a vacuum is usually sufficient to keep the pillars 68 in place.

Another method for arranging MLC elements 68 in the required matrix configuration is to dispose elements in a positioning and maintaining tool (not shown) having a waffle shaped bottom surface wherein each recess in the surface corresponds to the MLC front face and a central vacuum hole is provided for maintaining the MLC in place. The square front shape of MLC pillars 68 makes easier the alignment of the devices in the positioning and maintaining tool. Such a maintaining tool can be obtained by an electro-erosion process, or by molding, if polymer is used. However, such a waffle-shaped nevertheless has some disadvantages. For example, a kerf defined by the waffle lattice is predetermined and any change in this parameter will require either a new tool or result in excessive play in the position of the MLC pillars 68 so that possible rotation or misalignment thereof could occur.

Continuing with a consideration of the method of the second preferred embodiment, once all MLC pillars are mounted into the assembling tool 80, the connection wires 71 are held vertically and a flexible resin 88 is fed into the lattice formed by the MLC pillars 68. The resin 88 is fed at the sides of the array and the complete filling of the cavities or grooves between the pillars 68 is then accomplished by capillarity forces developed by the surface tension created on the walls forming the grooves. Further, the assembling tool 80 (FIG. 17) is preferably provided with lateral retaining walls (not shown) to contain resin in the matrix area. This method is similar to that used in "dice and fill" composite fabrication. A suitable resin for pillar lattice filling is preferably chosen from groups including rubbers or polyurethane or silicone, among others.

After the resin is applied, curing is then carried out to more definitively secure pillars in the matrix.

In a further step, backing material may be poured on the rear face of the matrix. Pouring of the backing is the presently preferred method because of the large number of wires extending outwardly at this side of the array. As indicated above, the backing materials is preferably obtained from mixing of resin and mineral and metallic particles. This provides the material with the high acoustic impedance and large attenuation coefficient necessary to eliminate acoustic reflections from the rear face of the piezoelectric members.

Curing of the backing is a delicate operation and should be carried out with strict observation of the operating conditions. The curing status of the resin will dramatically impact on the success of the operations to come. Once the backing is completely cured, the resultant transducer device so obtained is then removed from the positioning and maintaining tool 80 and the wires 71 are connected to a printed circuit board (not shown). Each element of the array is defined by a pair of wires corresponding, respectively, to the two polarities of the transducer. At this stage, the final number of transducers forming the matrix array can be determined based on the wires extending from the rear face of transducer. However, the front face of the array still has an intermediate number of elements corresponding to the assembled MLC pillars.

Figure 16:
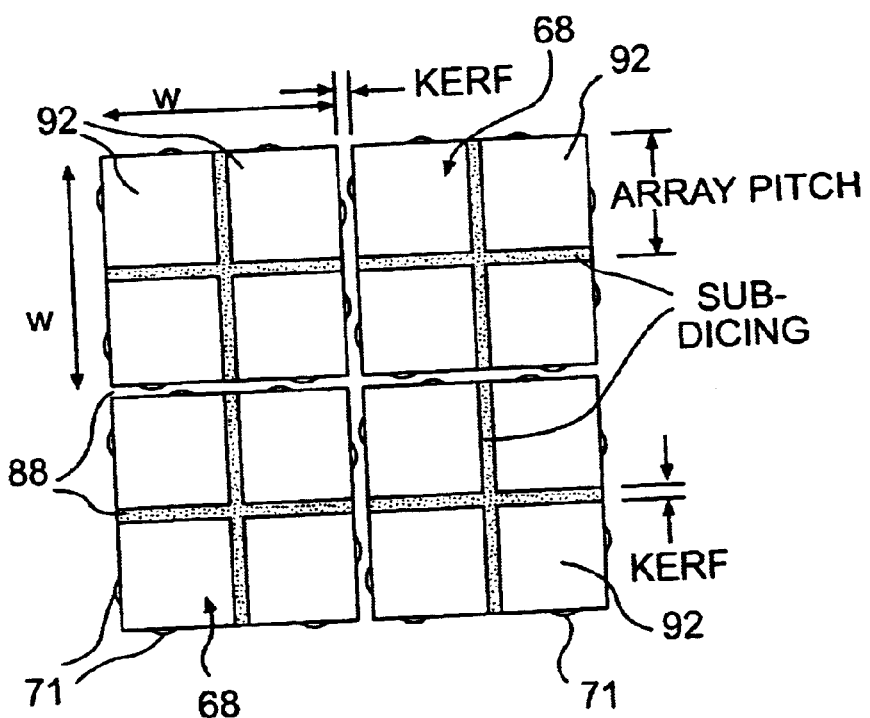
FIG. 16 is a view similar to that of FIG. 13, after subdicing.

In FIG. 16, the sub-dicing of the matrix is indicated at 90, and grooves with the same width as the kerf of the array are obtained by, preferably, diamond blade cutting. Thereafter, each MLC pillar is separated into four quarters 92, each corresponding to a single transducer element of the matrix array. As indicated above, because the positioning holes 76 shown in FIG. 16 are located on the cutting axis 78, holes 76 are thus removed by the dicing action. Preferably, the cutting should penetrate through the thickness of MLC to partially slice the backing layer. In this way, each elemental transducer 92 can be made more vibration independent so that cross coupling is reduced. In addition, the resultant grooves are preferably filled by the same resin that has been previously used for filling the lattice of MLC pillars in order to preserve good homogeneity throughout the array. Curing of this filling resin finalizes the assembly of the matrix array multilayer transducer.

Matching layers (not shown) corresponding to those discussed above can be advantageously added on the front surface of the array to optimize the energy transfer to the medium of concern. A focusing lens (not shown) also corresponding to that described above, can also be provided as desired.

It is believed that matrix transducer arrays fabricated using MLC technology as described above should be more competitive than arrays obtained from single layer piezoelectric, and should be instrumental in the realization of modern 2D array imaging transducers. Transducers of this type have been investigated and developed over several years but those developed prior to the present invention still produce a limited quality image in comparison with that produced by 1D arrays.

Although the invention has been described above in relation to preferred embodiments thereof, it will be understood by those skilled in the art that variations and modifications can be effected in these preferred embodiments without departing from the scope and spirit of the invention.

What is claimed:

1. An ultrasonic 1.5D transducer array for imaging applications, said array including a plurality of rows of elemental transducers, and said elemental transducers of the array being made up of a plurality of layers of a piezoelectric ceramic, and the array further including impedance compensation means for providing electrical impedance compensation between different rows of the transducers comprising the array so as to compensate for differences in impedance that would otherwise exist between the different rows of the transducers, and means for electrically connecting the transducers of each row independently of each other and for electrically connecting in parallel the layers of piezoelectric ceramic forming the elemental transducers.

2. A transducer array according to claim 1 wherein the layers are made from a composition selected from the group consisting of ceramic, a polymer-ceramic composite, a piezoelectric polymer, a single crystal, and a polymer-single crystal composite.

3. A transducer array according to claim 1 wherein said impedance compensation means is provided by selection of the number of layers for each row of the array according to the difference in impedance between rows in the elevation plane of the array.

4. A transducer array according to claim 1 wherein the row of the plurality of rows having the highest capacitance is comprised of a single layer piezoelectric material and adjacent rows are comprised of a multilayer piezoelectric material.

5. A transducer array according to claim 4 wherein the highest capacitance row is a central row and adjacent rows having equal numbers of layers are disposed on both sides of the central row.

6. A method for producing an ultrasonic multilayer row for a 1.5D transducer array, said array having a pitch, and said method comprising:

providing a plurality of piezoelectric layers to form a vibrating member having a thickness corresponding to a desired transducer frequency;

assembling said plurality of layers in reversed polarity to each other to form a parallel electrical circuit;

providing each layer with two opposed electrodes having outwardly extending conductive lines on opposite lateral faces thereof;

providing a set of flexible circuits having conductive traces thereon spaced apart by an amount equal to twice the pitch of the array, and disposing said circuits on the opposite lateral faces of said layers so as to connect together all of the conductive lines of said layers; and bonding said flexible circuits on said opposite lateral faces to the conductive lines at the respective lateral faces.

7. A method for producing a final multilayer ultrasonic matrix transducer array, said method comprising:

providing a plurality of multilayer piezoelectric elements of larger dimensions than those of the final array, said multilayer piezoelectric elements including electrical connection wires located around the periphery thereof, and positioning holes located on front surfaces thereof;

disposing said multilayer piezoelectric elements on a positioning surface to form an intermediate matrix array having the same overall dimensions as and a smaller number of elements than the final array;

encapsulating the intermediate array of multilayer elements with a polymeric resin to maintain said elements in place;

providing a backing on one side of the intermediate matrix array;

sub-dicing the multilayer elements of the intermediate array in quarters to produce the final multilayer matrix transducer array;

filling dicing grooves formed by said sub-dicing with a flexible resin; and connecting the final matrix transducer array to cables.

8. A method according to claim 7 further comprising providing an acoustic lens on a side array opposed to said one side.

9. A method according to claim 7 wherein said positioning surface is part of a positioning tool.

10. A method according to claim 7 wherein a tool plate including said positioning surface is used to form said matrix array and said tool includes pins corresponding to positioning holes for facilitating alignment of the matrix array.

11. A matrix array according to claim 7 wherein said positioning holes are disposed on two crossing axes of said front surfaces.

12. A method according to claim 7 wherein said positioning holes are of a shape selected from the group consisting of circular, oval, triangular and rectangular.

13. A method according to claim 7 wherein said holes are produced by one of laser machining, mechanical drilling and ultrasonic machining.

14. A method according to claim 7 wherein the transducer array has four lateral faces, electrode wires are disposed on said four lateral faces, each lateral face includes at least two electrode wires connected in parallel, and the polarity of the electrode wires is reversed for adjacent faces of the device.

15. A method according to claim 7 wherein wire solder pads are located on lateral surfaces of the elements at positions, and with a spacing between said pads, such that electrical shunting between adjacent elements is avoided.

16. A method according to claim 7 wherein the multilayer elements are disposed on a waffle shaped surface of a tooling plate to provide alignment of the elements.

17. A method according to claim 7 wherein the multilayer elements forming the transducer array are of rectangular cross-sectional shape.

18. A method according to claim 7 wherein the multilayer elements forming the transducer array are of a square cross-sectional shape.

19. A method according to claim 7 wherein said multilayer piezoelectric elements are comprised of one of a PZT ceramic, and a polymer.

20. A method according to claim 7 wherein said multilayer piezoelectric elements are comprised of one of a single crystal and a composite.

* * * * *